(12) United States Patent
Pearce, III et al.

(10) Patent No.: US 8,956,340 B2
(45) Date of Patent: Feb. 17, 2015

(54) URETHRAL CATHETER ASSEMBLY WITH A GUIDE WIRE

(71) Applicants: William Lanier Pearce, III, Tampa, FL (US); Douglas A. Swartz, Jacksonville, FL (US)

(72) Inventors: William Lanier Pearce, III, Tampa, FL (US); Douglas A. Swartz, Jacksonville, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/103,313

(22) Filed: Dec. 11, 2013

(65) Prior Publication Data

US 2014/0171921 A1    Jun. 19, 2014

Related U.S. Application Data

(63) Continuation of application No. PCT/US2013/071788, filed on Nov. 26, 2013.

(60) Provisional application No. 61/736,745, filed on Dec. 13, 2012.

(51) Int. Cl.
*A61M 25/00* (2006.01)
*A61M 25/09* (2006.01)
(Continued)

(52) U.S. Cl.
CPC ....... *A61M 25/0017* (2013.01); *A61M 25/0102* (2013.01); *A61M 25/0147* (2013.01); *A61M 25/01* (2013.01); *A61M 25/0133* (2013.01);
(Continued)

(58) Field of Classification Search
CPC .......... A61M 25/002; A61M 25/0172; A61M 25/09; A61M 25/09016; A61M 25/09025; A61M 25/09033; A61M 25/09041; A61M 25/0905; A61M 2025/0063; A61M 2025/0186; A61M 2025/09; A61M 2210/1089; A61M 2210/1092; A61M 2210/1096; A61M 2025/0681; A61M 25/0606; A61M 25/0662; A61M 27/008; A61M 25/0102; A61M 2025/0004; A61M 25/0017; A61M 25/01; A61M 25/0063; A61M 25/0064; A61M 2025/0065; A61M 2025/09066; A61M 2025/09075; A61M 2025/09133; A61M 2025/0915; A61M 25/00; A61M 25/0041; A61M 25/005; A61M 25/0105; A61M 25/0133; A61M 25/0136; A61M 25/0147; A61M 25/0152; A61M 25/04; A61M 25/10

See application file for complete search history.

(56) References Cited

U.S. PATENT DOCUMENTS 4,497,324 A    2/1985 Sullivan et al.
4,582,181 A    4/1986 Samson
(Continued)

OTHER PUBLICATIONS

International Search Report for PCT/US2013/071788, International Filing date Nov. 26, 2013, with a mailing date of Mar. 10, 2014.

*Primary Examiner* — Adam Marcetich
(74) *Attorney, Agent, or Firm* — Nicholas Pfeifer; Smith & Hopen, P.A.

(57) ABSTRACT

A urethral catheter assembly utilizing a removable guide wire for navigating the catheter through a patient's urethral lumen during the insertion procedure. The guide wire being very flexible and having a low coefficient of friction, thus reducing the likelihood of injuring or puncturing the urethra during insertion. The guide wire extends beyond the distal end of the catheter assembly to ensure that the flexible tip of the guide wire is the first contact point between the catheter assembly and the urethral lumen. In one embodiment, the guide wire extends beyond the proximal end of the catheter assembly and is adapted to be handled by a medical doctor to manually maneuver the guide wire through the urethra.

11 Claims, 4 Drawing Sheets

(51) Int. Cl.
  *A61M 25/01* (2006.01)
  *A61M 25/06* (2006.01)
  *A61M 25/04* (2006.01)

(52) U.S. Cl.
  CPC ........ *A61M 2025/0064* (2013.01); *A61M 25/00* (2013.01); *A61M 25/0041* (2013.01); *A61M 2025/0186* (2013.01); *A61M 2025/0065* (2013.01); *A61M 2025/0681* (2013.01); *A61M 25/008* (2013.01); *A61M 2025/0063* (2013.01); *A61M 25/04* (2013.01); *A61M 25/09041* (2013.01); *A61M 2210/1092* (2013.01)
  USPC .................. 604/544; 604/540; 604/93.01

(56) References Cited

U.S. PATENT DOCUMENTS

| | | | |
|---|---|---|---|
| 4,655,750 A * | 4/1987 | Vaillancourt | 604/165.01 |
| 4,787,884 A * | 11/1988 | Goldberg | 604/8 |
| 4,863,431 A * | 9/1989 | Vaillancourt | 604/168.01 |
| 5,045,061 A | 9/1991 | Seifert et al. | |
| 5,263,931 A | 11/1993 | Miller | |
| 5,304,214 A * | 4/1994 | DeFord et al. | 607/105 |
| 5,318,535 A | 6/1994 | Miraki | |
| 5,366,441 A * | 11/1994 | Crawford | 604/510 |
| 5,484,384 A * | 1/1996 | Fearnot | 600/3 |
| 6,238,383 B1 * | 5/2001 | Karram et al. | 604/544 |
| 6,368,302 B1 | 4/2002 | Fitzmaurice et al. | |
| 6,398,780 B1 * | 6/2002 | Farley et al. | 606/41 |
| 6,428,563 B1 * | 8/2002 | Keller | 607/105 |
| 6,527,737 B2 | 3/2003 | Kaneshige | |
| 6,589,271 B1 * | 7/2003 | Tzeng et al. | 607/105 |
| 6,599,230 B2 * | 7/2003 | Hastings et al. | 600/3 |
| 7,780,650 B2 * | 8/2010 | Frassica et al. | 604/544 |
| 8,377,041 B2 * | 2/2013 | Frassica et al. | 604/544 |
| 2001/0014790 A1 * | 8/2001 | Heller et al. | 604/194 |
| 2002/0038115 A1 * | 3/2002 | Dulak et al. | 604/544 |
| 2007/0060908 A1 * | 3/2007 | Webster et al. | 604/509 |
| 2007/0078446 A1 * | 4/2007 | Lavelle | 606/1 |
| 2009/0143768 A1 * | 6/2009 | Parodi et al. | 604/528 |
| 2009/0275842 A1 * | 11/2009 | Saadat et al. | 600/478 |
| 2012/0035590 A1 * | 2/2012 | Whiting et al. | 604/528 |

* cited by examiner

URETHRAL CATHETER ASSEMBLY WITH A GUIDE WIRE

CROSS-REFERENCE TO RELATED APPLICATIONS

This nonprovisional application is a continuation of currently pending PCT Application No. PCT/US13/71788 filed Nov. 26, 2013, which claims priority to provisional application No. 61/736,745, entitled "URETHRAL CATHETER ASSEMBLY WITH A GUIDE WIRE," filed Dec. 13, 2012 by the same inventor; the contents of which are hereby incorporated by reference.

FIELD OF INVENTION

The invention relates generally to the field of medical devices, and specifically, to urethral catheters.

BACKGROUND

Urethral catheterization is a routine procedure, which allows drainage of the bladder. Although the procedure is very common, catheter insertion may be difficult and may cause urethral injury. Traditional catheters currently used are generally blunt, difficult to insert, and are prone to damaging urethral walls. These problems are prevalent for both male and female patients and constitute a significant concern.

As evidenced by some reports, nearly 10% of male catheter insertions result in trauma requiring a urology consult and resulting in unnecessary operations. In males, the urethra is a narrow muscular tube that extends from the tip of the penis through the prostate into the bladder and is about 20-24 cm long and has a thin wall of about only 3 mm. Often, permanent damage is caused by the false passage of improper insertion. In many cases, a catheter cannot be properly placed in a male, necessitating delay while a consult is obtained. In males, the primary source of catheterization complications is due to enlarged prostate and pre-existing urethral strictures.

Catheterization in females may also be difficult and cause injuries. Females have small urethral openings through which insertion of a typical blunt catheter may be problematic. The procedure is often painful for the patients and difficult to perform for the medical practitioners. The common practice after encountering a difficulty inserting a catheter is continuing attempts by applying more force or using another similar blunt-tipped catheter. This often leads to unnecessary trauma.

One known method of inserting a catheter in problematic cases requires a dilation device. Existing dilation devices utilize guide wires for insertion. The dilation devices are used to expand the urethral lumen to allow for passage of a catheter. This procedure, however, has several significant shortcomings. The only commercially available devices use guide wires made of stiff metal, and therefore, frequently puncture patients' urethras. In addition, the complexity of these devices limits their utility because only licensed physicians are authorized to use them. In addition, urinary tract infection is a serious concern associated with catheters. Using dilation devices increases a patient's risk of urinary tract infection because the dilation device must be inserted and removed before the catheter may be inserted, thus increasing the likelihood of UTI.

Accordingly, there is a need for a urethral catheter with a flexible guide wire to facilitate a safer and easier catheterization. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF INVENTION

The long-standing but heretofore unfulfilled need for a urethral catheter which may be safely guided through a patient's urethra using a flexible guide wire is now met by a new, useful, and nonobvious invention.

This invention comprises an open ended hollow rubber tube adapted to function as a catheter to drain the patient's bladder. This catheter may also contain an inflatable balloon positioned at its distal end to facilitate retention of the catheter in the bladder. A smaller plastic sheath may be inserted through the lumen of the catheter; the plastic sheath may slightly protrude from the tip of the catheter. A flexible guide wire is inserted through the lumen of the sheath and extends beyond the distal end thereof. The guide wire preferably has a very low coefficient of friction, especially when its surface is exposed to a liquid. One acceptable material for the guide wire is nickel titanium, but any material with similar properties—high flexibility and low coefficient of friction—may be used.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The urethral catheter assembly according to the present invention constitutes a major improvement over the prior art. The catheter assembly includes an elongated catheter body housing a guide wire sheath which is capable of receiving a guide wire having a flexible and near frictionless distal end. The guide wire utilized in the catheter assembly serves a primary function of safely navigating the catheter through a patient's urethral lumen. The present invention decreases recurrent instrumentation, which greatly increases the risk of serious trauma or infection typically resulting from medical professionals struggling to insert traditional catheters into particularly narrow openings. Since the wire is very flexible and almost frictionless, the likelihood of damaging the urethral lumen is greatly reduced. The guide wire is removably assembled allowing for a perfectly placed catheter without the risk of complications stemming from the guide wire remaining in the patient's body.

EXAMPLE

Figure 1:
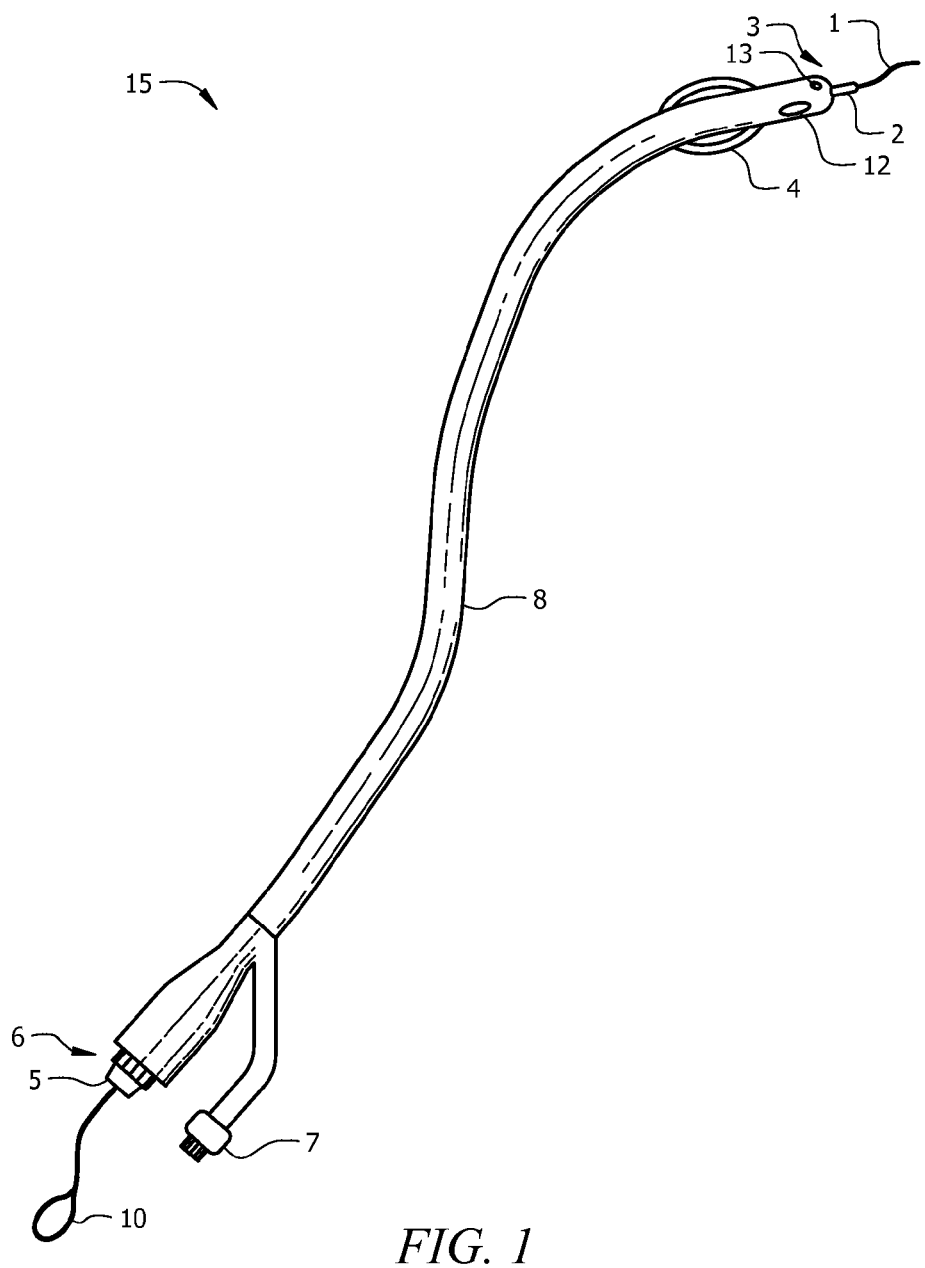
FIG. 1 is a perspective view of a first embodiment of the catheter assembly with a guide wire.

Referring to FIG. 1, a first embodiment, generally referred to by element number 15, of the catheter assembly according to the present invention includes catheter body 8, guide wire 11 (See FIG. 3), and a guide wire sheath. Catheter body 8 is a hollow flexible tubular member made out of rubber or another material, known by a person having ordinary skill in the art, which contains similar properties. Catheter body 8 includes proximal end 6 and distal end 3, where distal end 3 is capable of being inserted into an opening in a patient's body, preferably a urethra.

Catheter body 8 houses the guide wire sheath, which has first end 2 and a second end (not shown). The sheath extends longitudinally through the entire length of catheter body 8, such that first end 2 may protrude through distal end 3 of catheter body 8 and the second end is attached to proximal plug 5, which is removably attached to proximal end 6 of catheter body 8. Proximal plug 5 provides the user with a means to easily detach the sheath from the catheter body. In a certain embodiment, first end 2 of the guide wire sheath extends outward about 2.5 cm from distal end 3 of catheter body 8.

Figure 3:
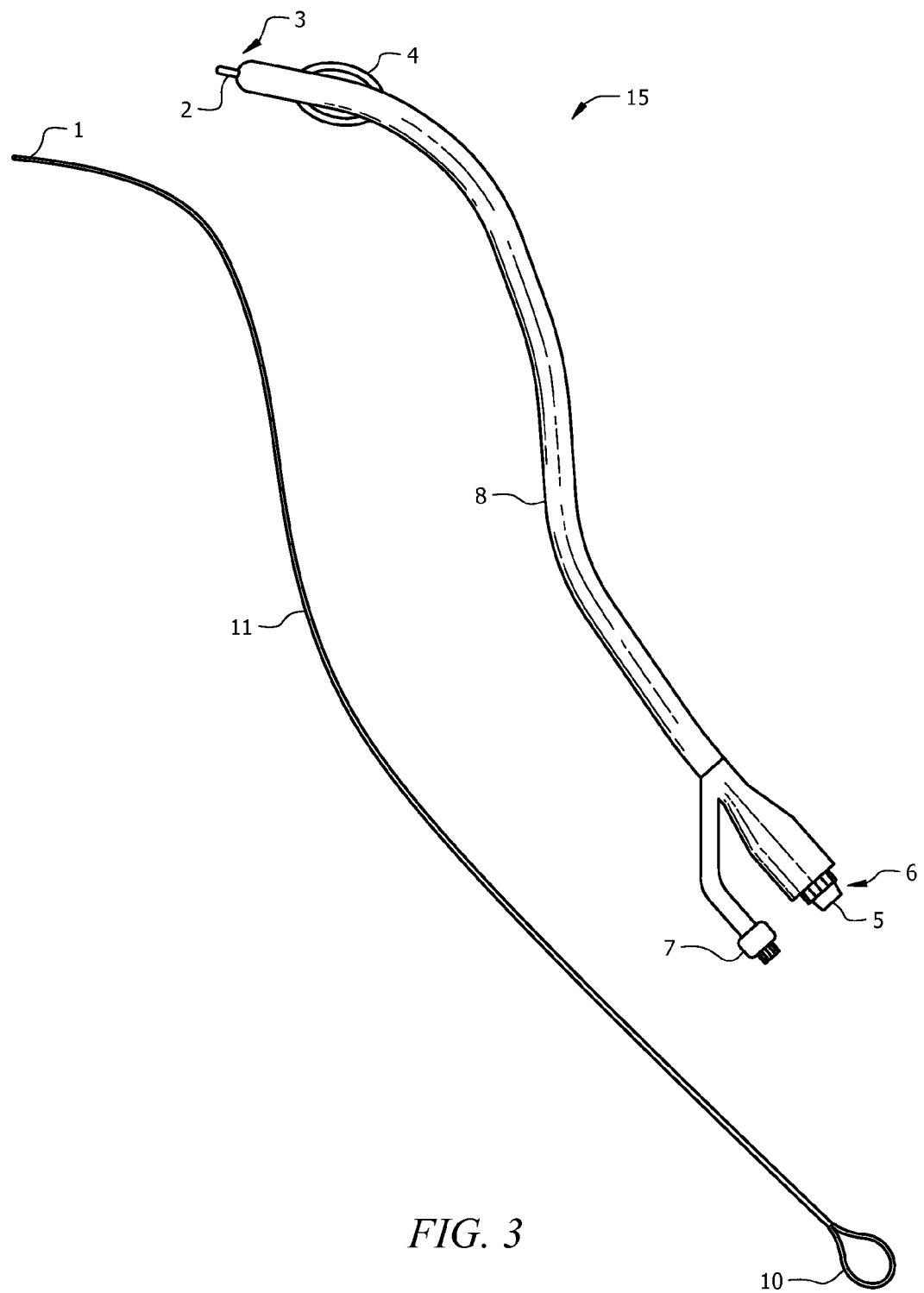
FIG. 3 is a perspective view of the first embodiment of the catheter assembly with the guide wire removed.

Guide wire 11, shown separately from embodiment 15 in FIG. 3, is housed within the guide wire sheath and includes distal end 1 and proximal end 10, where at least some portion of distal end 1 is made of a material providing high flexibility and a low coefficient of friction. One such material suitable for distal end 1 of guide wire 11 is nickel titanium, but a person having ordinary skill in the art may use another material that contains similar properties—flexibility and low coefficient of friction. Distal end 1 of guide wire 11, is inserted through proximal plug 5 and into the guide wire sheath with at least some amount of distal end 1 of guide wire 11 protruding from first end 2 of the guide wire sheath. In one embodiment the flexible portion may be about 0.5 to about 0.75 cm in length and distal end 1 of guide wire 11 preferably extends beyond guide wire sheath 2 by about 3 cm. Proximal end 10 of guide wire 11 is more rigid than distal end 1 of guide wire 11 and guide wire proximal end 10 extends outward beyond proximal end 6 of catheter body 8. The healthcare provider may hold and manually maneuver proximal end 10 of guide wire 11 when maneuvering the catheter. A certain embodiment may contain a handle-like feature for easier control. The operation of this embodiment is more complex, and therefore, it is intended to be used by medical doctors.

Figure 2:
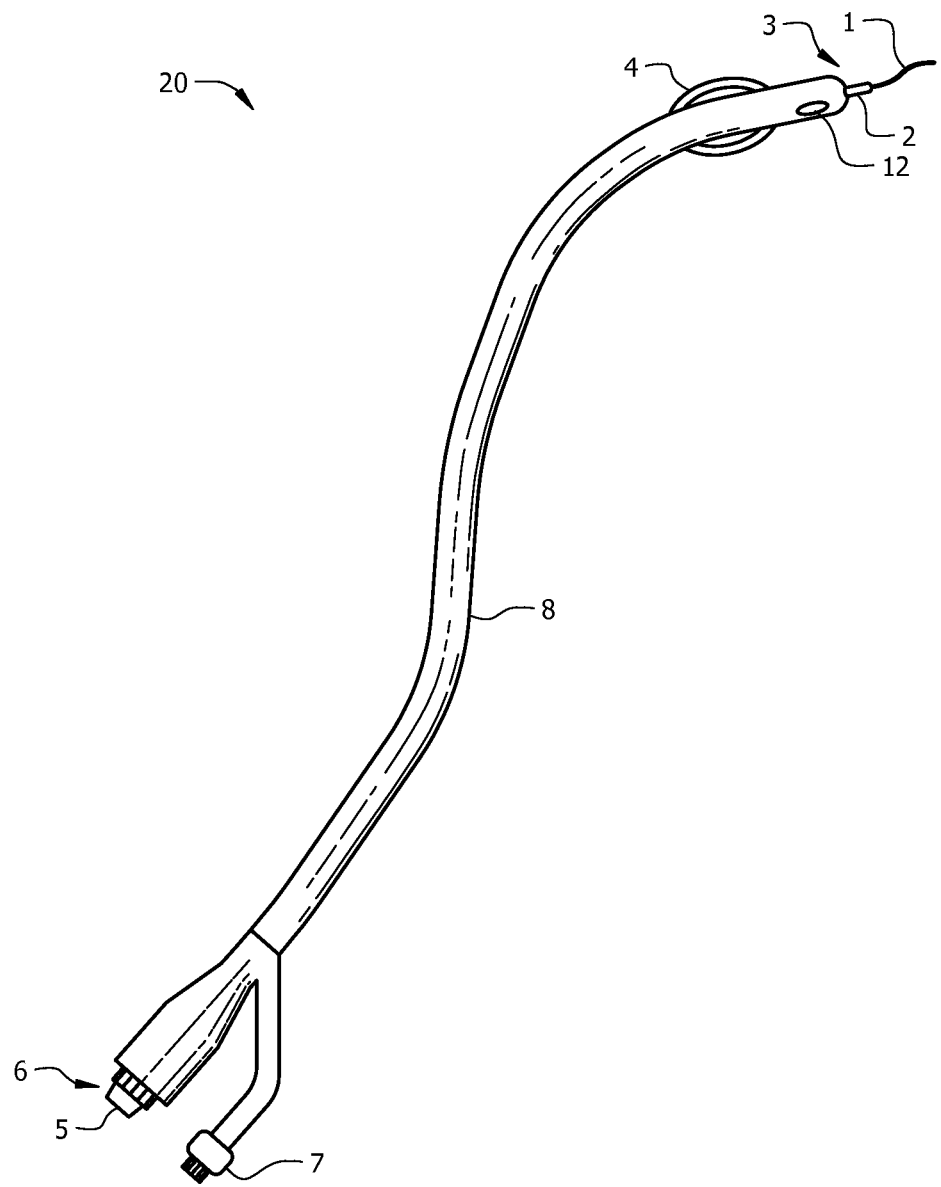
FIG. 2 is a perspective view of a second embodiment of the catheter assembly with a guide wire.

According to a second embodiment of the catheter assembly, generally denoted as 20 and depicted in FIG. 2, proximal end 10 of guide wire 11 does not extend beyond proximal plug 5. Additionally, proximal end 10 of guide wire 11 is attached to proximal plug 5 along with the second end of the guide wire sheath so that guide wire 11 cannot be manipulated by the user, but can still easily be removed. This simplified embodiment of the invention is intended to be used primarily by nurses and other medical personnel.

As seen in FIGS. 1-3, the catheter assembly may also include inflatable balloon 4 at distal end 3 of catheter body 8 which may be inflated by a balloon pump attachable to balloon pump access 7. Moreover, the catheter assembly may contain drainage aperture 12, shown in FIGS. 1-2, connected to a drainage lumen (not shown) on the interior of catheter body 8 to allow internal bodily fluids to enter through drainage aperture 12, pass through the drainage lumen, and exit the patient's body.

Figure 4:
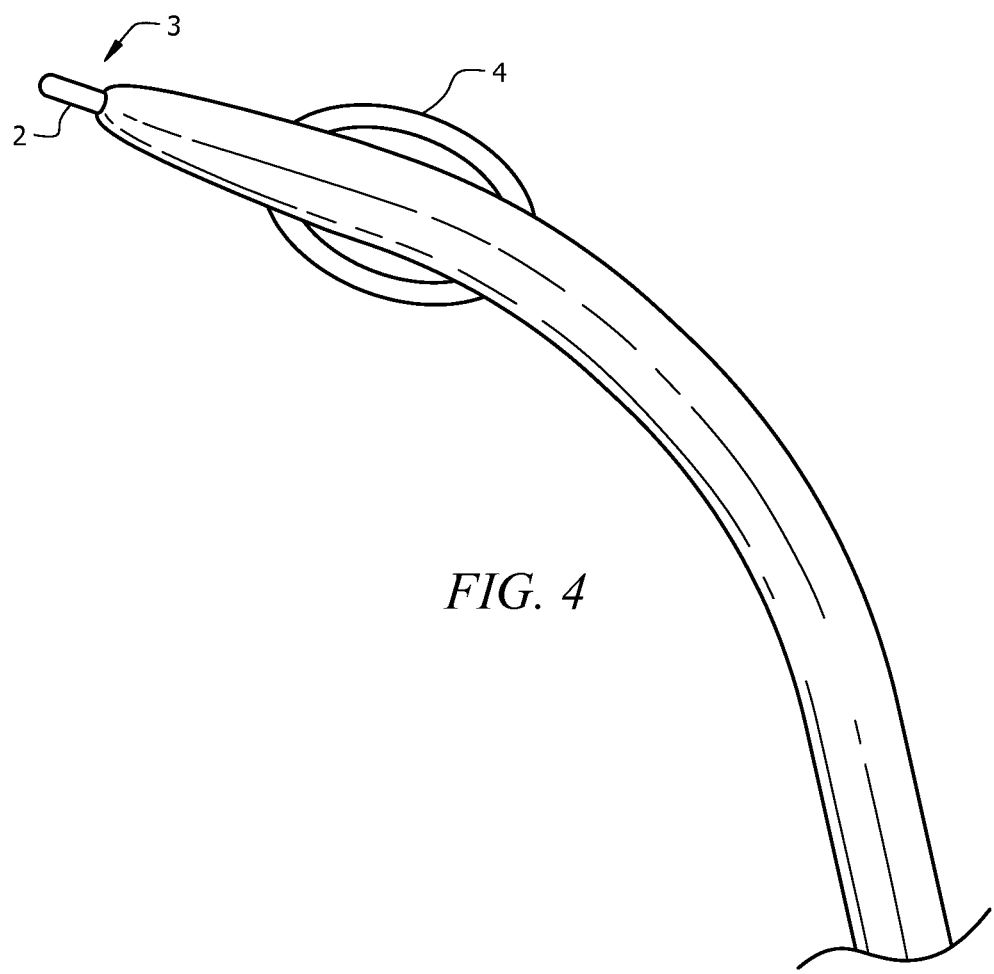
FIG. 4 is a close-up view of the distal end of the catheter body illustrating a tapered distal end.

As shown in FIG. 4, a certain embodiment may utilize a catheter body having a tapered distal end to allow for easier bodily insertion with reduced risk of trauma to the patient's body.

In a certain embodiment, catheter body 8 may contain electronics mount 13 that allows for the attachment of desired electronics near distal end 3 of catheter body 8, including but not limited to, imaging devices, flashlights, or sensors. See FIG. 1.

In both embodiments, after the catheter is successfully inserted and secured within the bladder, both the guide wire and the sheath are removed through the proximal end of the catheter. One clear advantage of the urethral catheter assembly according to the present invention is its simplicity. The second embodiment is a simple one-piece instrument suitable for use by nurses, while the first embodiment is a more complex device having the same functionality, but in addition, allowing doctors to manually manipulate the guide wire through the urethra. In a certain embodiment the proximal plug may be attachable to the guide wire so that the guide wire can be manipulated by a doctor when not attached, but also allows the guide wire to attach to the proximal plug if a nurse were to use the catheter assembly.

The present invention allows a urethral catheter to be inserted into the bladder with less risk of trauma from multiple insertion attempts and less risk of puncturing the urethra wall from a less flexible guide wire than currently available models. The catheter assembly according to the present invention also allows the catheter to pass more easily through strictures, or other urethral and prostatic trauma, with less risk of further damage than the devices currently known in the art.

GLOSSARY OF CLAIM TERMS

Balloon Pump Access: is a connection point capable of communicating with a balloon pump.

Balloon Pump: is a device capable of filing a balloon with a gas or fluid.

Balloon: is an inflatable structure attachable to a distal end of a catheter body that is insertable into a body cavity or structure and capable of being distended with gas or fluid.

Electronic Mount: is an attachment point for electronic devices that a user may desire to be located on the generally distal end of a catheter body.

Guide Wire Sheath: is an elongated enveloping tubular structure designed to house a guide wire.

Guide Wire: is a thin partially flexible wire that can be inserted into a confined or tortuous space to act as a guide for subsequent insertion of a stiffer or bulkier instrument.

Proximal Plug: is a coupling device typically located near the proximal end of a catheter which removably secures the guide wire sheath to the catheter body.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A urethra or bladder catheter assembly having fixed length components with a fixed guide wire to enable professionals not trained in catheter insertion to safely insert the catheter into a patient's body without the risk of puncturing a lumen wall, comprising:
   components with fixed lengths, wherein the components include an elongated tubular catheter body, a guide wire sheath, and a guide wire;
   the elongated tubular catheter body having a predetermined fixed length, a distal end, a proximal end, and a width, wherein the distal end and width are complimentary for insertion into a patient's urethra or bladder;
   a guide wire sheath housed within the catheter body, wherein the guide wire sheath has a predetermined length, a first end, and a second end, the first end generally located towards the distal end of the catheter body and the second end generally located towards the proximal end of the catheter body;
   a guide wire having a predetermined length, a distal end, and a proximal end, the distal end further including:
      at least some portion being flexible;
      being generally located towards the distal end of the catheter body and the first end of the guide wire sheath when the catheter assembly is assembled;
      the length being greater than the length of the guide wire sheath;
   the guide wire sheath capable of receiving the guide wire;
   the proximal end of the catheter body adapted to receive the guide wire sheath and the guide wire, the distal end of the catheter body adapted to allow at least some portion of the distal end of the guide wire to exit the catheter body;
   a proximal plug that removably attaches the second end of the sheath to the proximal end of the catheter body; and
   the guide wire permanently attached to the proximal plug such that a fixed length of guide wire extends from the distal end of the catheter and the distal end of the sheath, thereby preventing an operator from adjusting the length of guide wire extending from the distal end of the catheter and the distal end of the sheath during the insertion of the catheter into the patient's urethra or bladder.

2. The urethra or bladder catheter assembly according to claim 1, further comprising:
   a balloon pump access connected to the catheter body generally near the proximal end of the catheter body.

3. The urethra or bladder catheter assembly according to claim 2, further comprising:
   a balloon positioned at the distal end of the catheter body, the balloon being inflatable by a balloon pump connected to the balloon pump access, wherein the balloon is deflated during the insertion of the catheter assembly into the patient's body.

4. The urethra or bladder catheter assembly according to claim 1, further comprising:
   the distal end of the catheter body adapted to allow at least some portion of the second end of the sheath and the distal end of the guide wire to exit the catheter body.

5. The urethra or bladder catheter assembly according to claim 1, further comprising:
   the distal end of the catheter body being tapered to allow for easier insertion into the patient's body.

6. The urethra or bladder catheter assembly according to claim 1, further comprising:
   the catheter body adapted to allow at least some portion of the first end of the sheath to exit the catheter body, and the length of the sheath being greater than the length of the catheter body such that the first end of the sheath extends outward a predetermined distance from the distal end of the catheter body.

7. The urethra or bladder catheter assembly according to claim 1, further comprising:
   the guide wire having a coefficient of friction that enables the guide wire to easily move through a patient's body without causing trauma to the patient's body during insertion of the guide wire.

8. The urethra or bladder catheter assembly according to claim 1, further comprising:
   the flexible portion of the distal end of the guide wire having a nickel titanium composition.

9. The urethra or bladder catheter assembly according to claim 1, further comprising:
   the distal end of the catheter body having a drainage aperture connected to a lumen disposed throughout the catheter body allowing fluid to exit the patient's body.

10. The urethra or bladder catheter assembly according to claim 1, further comprising:
    the length of the guide wire sheath being equal to or longer than the catheter body's length.

11. The urethra or bladder catheter assembly according to claim 1, further comprising:
    an electronic mount generally located towards the distal end of the catheter body to provide a user with an attachment point for attaching electronic devices.

* * * * *